United States Patent [19]
Tachikawa et al.

[11] Patent Number: 5,994,573
[45] Date of Patent: Nov. 30, 1999

[54] METHOD FOR MAKING TRIARYLAMINE COMPOUNDS HAVING HYDROCARBONOXYSILYL GROUPS

[75] Inventors: Mamoru Tachikawa; Kasumi Takei, both of Kanagawa, Japan

[73] Assignee: Dow Corning Asia, Ltd., Tokyo, Japan

[21] Appl. No.: 09/220,122

[22] Filed: Dec. 23, 1998

[30] Foreign Application Priority Data

Dec. 24, 1997 [JP] Japan ................................. 9-355210
Jun. 26, 1998 [JP] Japan ................................. 10-180997

[51] Int. Cl.$^6$ ................................. C07F 7/08; C07F 7/10
[52] U.S. Cl. ................................. 556/479; 556/413
[58] Field of Search ................................. 556/413, 479

[56] References Cited

U.S. PATENT DOCUMENTS

| | | | |
|---|---|---|---|
| 4,599,394 | 7/1986 | Lucas | 528/15 |
| 4,614,812 | 9/1986 | Schilling, Jr. | 556/406 |
| 4,904,723 | 2/1990 | Iwahara et al. | 525/100 |
| 5,424,470 | 6/1995 | Bank et al. | 556/479 |
| 5,449,802 | 9/1995 | Bank et al. | 556/479 |
| 5,481,016 | 1/1996 | Bank et al. | 556/479 |
| 5,486,637 | 1/1996 | Bank et al. | 556/479 |
| 5,616,763 | 4/1997 | Bank et al. | 556/479 |

FOREIGN PATENT DOCUMENTS

| | | |
|---|---|---|
| 57-190043 | 5/1981 | Japan . |
| 63-6041 | 6/1986 | Japan . |

*Primary Examiner*—Paul F. Shaver
*Attorney, Agent, or Firm*—William F. Boley

[57] ABSTRACT

A method for making a triarylamine having a hydrocarbon oxysilyl group SiOR', where R' is an organic group comprising 1 to 10 carbon atoms, which is important as a hole transfer substance in electronic applications, at a high yield and high position selectivity, comprising reacting a hydrido (hydrocarbonoxy)silane compound with a triarylamine having a vinyl group in the presence of platinum or platinum compound catalyst and a carboxylic acid compound.

14 Claims, No Drawings

METHOD FOR MAKING TRIARYLAMINE COMPOUNDS HAVING HYDROCARBONOXYSILYL GROUPS

BACKGROUND OF INVENTION

The present invention is a method for making a triarylamine compound having hydrocarbonoxysily groups, which is useful in charge transfer materials and the like used in photosensitive materials for electronic photography. Triarylamines are important materials as charge transfer substances and in particular those having hydrocarbonoxysilyl groups have the following advantages over those not having hydrocarbonoxysilyl groups: (1) the characteristics attributable to the hydrocarbonoxysilyl groups are imparted to the surface characteristics of a charge transfer material, (2) miscibility with silicon-based materials is good, (3) silicon-oxygen bonds are easier to form on an inorganic material surface, and (4) it is possible to effect curing by the formation of a crosslinked structure resulting from silicon-oxygen bonds.

The following are the most common methods for manufacturing a triarylamine having hydrocarbonoxysilyl groups.

1) Organometal reagent method: This process includes a Grignard method in which an organometal reagent is prepared by a reaction between a halogen derivative of a triarylamine and metallic magnesium and this product is allowed to react with chlorosilane or an alkoxysilane to form silicon-oxygen bonds; and an organolithium method in which a lithium reagent is used in place of the above-mentioned metallic magnesium.

2) Hydrosilylation method: One such hydrosilylation method involves allowing a triarylamine having unsaturated groups to react with a hydride silane compound to form silicon-oxygen bonds.

In method 1 above a Grignard method is particularly common, but has the following problems:

1) the above-mentioned halogen derivative used as a raw material is not easy to obtain because it is difficult to manufacture,
2) because an equivalent reaction is involved the cost of synthesis is high, and
3) a refining step is required because by-products occur.

A drawback to the hydrosilylation method is that a catalyst is needed, but in principle there are no by-products thus making this method a more desirable industrial process. There have been reports of methods for manufacturing a triarylamine having unsaturated groups by utilizing a hydrosilylation method. Even with this method, however, in actual practice the catalyst activity and the selectivity are low and oxygen must be added to the reaction atmosphere in order to prevent a decrease in the activity of the hydrosilylation catalyst. A number of problems are encountered in the hydrosilylation method such as (a) a large amount of catalyst is required and the reaction takes a long time, (b) reactions other than a hydrosilylation reaction can occur simultaneously forming polymers and producing oxides which lowers the yield, (c) the selectivity is low for the position where the addition is made in the hydrosilylation reaction and as a result the yield is low, (d) it is frequently difficult to separate and remove the by-products in the case of a low yield, and (e) there is the danger that the oxygen which it is often required to add will ignite and explode. Also because of the low selectivity for the position where the addition is made in the hydrosilylation reaction, a triarylamine having unsaturated groups obtained from this reaction will be a mixture of isomers. This mixture of isomers creates such problems as a difference among isomers in the decomposition and condensation rates of the hydrolyzable groups and a difference among isomers in the charge transfer capability due to varying ionization potential which is in turn due to different molecular structures.

An object of the present invention is to provide a novel method suited to the industrial production of a triarylamine having hydrocarbonoxysilyl groups by a hydrosilylation reaction. Specifically, an object is to solve the above identified problems (a) to (d) encountered with hydrosilylation reactions by increasing the activity of the platinum catalyst in a hydrosilylation reaction between a triarylamine compound having a vinyl group and a hydrido (hydrocarbonoxy) silane compound and improving the position selectivity thereby providing a method with which the targeted substance can be synthesized at a higher purity, at lower cost, and more efficiently. Another object is to provide a method in which the activity of the platinum catalyst is improved, which makes it possible for the hydrosilylation reaction to be conducted at a lower oxygen partial pressure or in an inert atmosphere and allows the danger of ignition and explosion during the hydrosilylation reaction to be avoided.

"Raising the position selectivity" here means that of the triarylamines having hydrocarbon oxysilyl groups that are the product, a triarylamine having a structure in which the hydrocarbonoxysilyl groups are bonded with aromatic rings via ethylene groups, that is, a β-adduct with respect to an aromatic ring can be produced more efficiently than in the past.

SUMMARY OF INVENTION

A method for making a triarylamine compound having a hydrocarbonoxysilyl group SiOR', where R' is an organic group comprising 1 to 10 carbon atoms, which is important as a charge transfer substance in electronic applications, at a high yield and high position selectivity, comprising reacting a hydrido (hydrocarbonoxy)silane compound with a triarylamine having a vinyl group in the presence of platinum or platinum compound catalyst and a carboxylic acid compound.

DESCRIPTION OF INVENTION

The present invention is a method for making a triarylamine compound having hydrocarbonoxysilyl groups comprising reacting a hydrido (hydrocarbonoxy)silane described by formula $$HR_nSi(OR')_{3-n} \qquad (1),$$

with a triarylamine compound having at least one triarylamine structure per molecule described by formula (Chemical Formula 2)

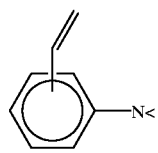

in the presence of platinum or platinum compound catalyst and a carboxylic acid compound; where each R is an independently selected hydrocarbon group selected from the group consisting of hydrocarbon groups comprising 1 to 10 carbon atoms and hydrocarbon groups comprising 1 to 10 carbon atoms in which at least one of the carbon atoms is bonded to a hetero-atom selected from the group consisting of O, N, F, Cl, Br, I, S, and Si; each R' is an independently selected hydrocarbon group comprising 1 to 10 carbon atoms; and n=0, 1, or 2; where the other bonds of the nitrogen atom are bonded to an aryl group.

Description of hydrido (hydrocarbonoxy)silane

The hydrido (hydrocarbonoxy)silane compound used in the present method is expressed by formula, $$HR_nSi(OR')_{3-n} \tag{1}$$

and is a silicon compound having a hydrogen atom bonded directly to a silicon atom, and at least one hydrocarbonoxy group expressed by OR' bonded to this silicon atom. The "Hydrocarbonoxy group" here is the portion corresponding to —OR' in Formula 1, and has a structure in which a hydrocarbon group is bonded to an oxygen atom which is bonded to a silicon atom. Mutually different hydrocarbonoxy groups may be bonded to the same silicon atom.

R' in Formula 1 is a hydrocarbon group comprising 1 to 10 carbon atoms, and each R group is and independently selected organic group selected from the group consisting of hydrocarbon groups comprising 1 to 10 carbon atoms and hydrocarbon groups comprising 1 to 10 carbon atoms and at least one of the carbon atoms is bonded to a hetero-atom selected from the group consisting of O, N, S, F, Cl, Br, I, and Si. The bonding position of the hetero-atom in the hydrocarbon group may be to a terminal group, a side chain, or the main chain skeleton.

Examples of R' include alkyl groups such as methyl, ethyl, n-propyl, isopropyl, n-butyl, t-butyl, pentyl, hexyl, octyl, and decyl; alkenyl groups such as 2-propenyl, hexenyl, and octenyl; aralkyl groups such as benzyl and phenethyl; and aryl groups such as phenyl, tolyl, and xylyl.

Examples of R include those given above for R', as well as groups such as chloromethyl, 4-chlorophenyl, trimethylsilylmethyl, and 2-methoxyethyl.

When n=2 in Formula 1 mutually different hydrocarbon groups (R) may be bonded to the same silicon atom. Of the above-mentioned hydrocarbon groups, it is preferable for R to be an alkyl group.

Specific examples of the hydrido (hydrocarbonoxy)silane compounds useful in the present method include the following: trihydrocarbon oxysilanes such as trialkoxysilanes, trialkenoxysilanes, and triaryloxysilanes, specific examples of which include trimethoxysilane, triethoxysilane, tri-n-propoxysilane, triisopropoxysilane, tributoxysilane, triisopropenoxysilane, and triphenoxysilane; dihydrocarbon oxysilanes such as dialkoxysilanes, dialkenoxysilanes, and diaryloxysilanes, specific examples of which include methyldimethoxysilane, methyldiethoxysilane, methyldi-n-propoxysilane, methyldiisopropenoxysilane, methyldiphenoxysilane, ethyldimethoxysilane, ethyldiethoxysilane, n-propyldimethoxysilane, n-propyldiethoxysilane, methyldioctyloxysilane, 3,3,3-trifluoropropyldimethoxysilane, 3,3,3-trifluoropropyldiethoxysilane, n-hexyldimethoxysilane, n-hexyldiethoxysilane, n-octyldimethoxysilane, n-octyldiethoxysilane, benzyldimethoxysilane, benzyldiethoxysilane, phenethyldimethoxysilane, phenethyldiethoxysilane, phenyldimethoxysilane, and phenyldiethoxysilane; monohydrocarbon oxysilanes such as monoalkoxysilanes, monoalkenoxysilanes, and monoaryloxysilanes, specific examples of which include dimethylmethoxysilane, dimethylethoxysilane, dimethyl-n-propoxysilane, dimethylisopropenoxysilane, dimethylphenoxysilane, diethylmethoxysilane, methylethylethoxysilane, n-propyl(methyl)methoxysilane, n-propyl(methyl)ethoxysilane, 3,3,3-trifluoropropyl(methyl)methoxysilane, bis(3,3,3-trifluoropropyl)ethoxysilane, n-hexyl(methyl)methoxysilane, di(n-hexyl)ethoxysilane, n-octyl(methyl)methoxysilane, di(n-octyl)ethoxysilane, benzyl(methyl)methoxysilane, phenethyl(methyl)methoxysilane, and methylphenylmethoxysilane; hydrocarbonoxysilanes having two or more hydrocarbonoxy groups with different structures such as alkoxy, alkenoxy, aralkyloxy, and aryloxy, such as methoxydiethoxysilane, diethoxypropenoxysilane, dimethoxyphenoxysilane, dimethoxybenzyloxysilane, diphenoxypropenoxysilane, and methylmethoxyphenethoxysilane; and those silane compounds in which R is a substituted group such as chloromethyl, 4-chlorophenyl, trimethylsilylmethyl, and 2-methoxyethyl.

The hydrido (hydrocarbonoxy)silane compounds are selected according to the reactivity thereof or as dictated by the intended application of the hydrocarbonoxysilyl functional polymer to be manufactured, but an alkoxysilane is usually preferable from the standpoint of reactivity.

Description of triarylamine compound

The present method requires a triarylamine compound having at least one triarylamine structure per molecule described by formula (Chemical Formula 2)

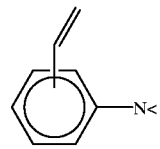

As used herein the term "triarylamine structure" refers to a structure in which all three bonds of a tertiary amine are bonded to an aryl group as illustrated in Chemical Formula 2. There may be one or more vinyl groups in the triarylamine structure having a vinyl group. There are no particular restrictions on the structure of the triarylamine compound having a vinyl group as long as it satisfies the above definition.

Examples of triarylamine compounds having a vinyl group include: (1) a compound that has just one triarylamine structure having a vinyl group and does not have any other triarylamine structure, (2) a compound that has two or more triarylamine structures having a vinyl group and does not have any other triarylamine structure, and (3) a compound having both a triarylamine structure having a vinyl group and a triarylamine structure not having a vinyl group.

The following are examples of the triarylamine structure of the triarylamine compound having a vinyl group.

(Chemical Formula 3)

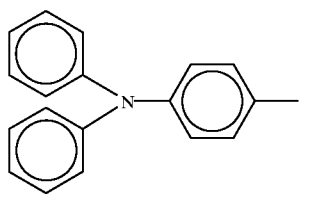

(I)

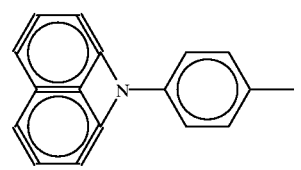

(II)

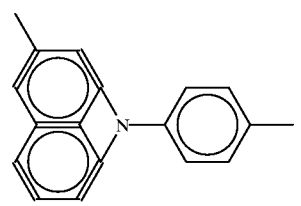

(III)

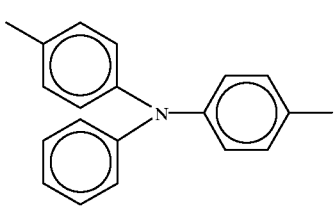

(IV)

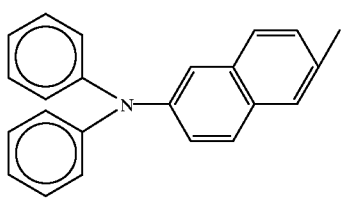

(V)

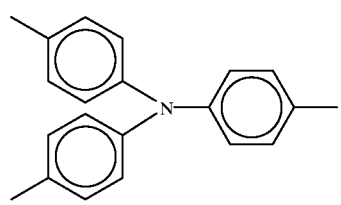

(VI)

In these formulas, free bonds (bonds where no substituent is depicted) represent bonds with other triarylamine structures. These bonds in the formulas are attached, for example, at the para position of the benzene ring with respect to the nitrogen atom, but may instead be at the meta or ortho position, and there are no particular restrictions on the attachment position in condensed rings, either. The para position is preferred, however, and in the case of a condensed ring, the position should be as far from the nitrogen atom as possible. In Formulas I, II, and V, there is only one bond, but there may be two or more of these bonds, as shown in Formulas III, IV, and VI, or there may be no bond. When there is no bond, this indicates that there is only one triarylamine structure. Furthermore, the hydrogen atoms of the benzene rings of these aryl groups may be substituted with, for example, a halogen atom or a methyl group. At least one of the triarylamine structures in the molecule of the above-mentioned triarylamine compound having a vinyl group is substituted with at least one vinyl group.

Of the aryl groups of the triarylamine compound having a vinyl group, specific examples include phenyl; a substituted phenyl such as a methyl substituted phenyl, for example, ortho-tolyl, meta-tolyl, para-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,5-trimethylphenyl, mesityl, or 3,4,5-trimethylphenyl; an ethyl substituted phenyl, such as a 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2,3,4-triethylphenyl, 2,3,5-triethylphenyl, 2,3,6-triethylphenyl, 2,4,5-triethylphenyl, 2,4,6-triethylphenyl, or 3,4,5-riethylphenyl; a mixed ethylmethyl substituted phenyl, such as a 3-ethyl4-methylphenyl, 3-ethyl-5-methylphenyl, 2,3-diethyl-4-methylphenyl, 2-ethyl-3,5-dimethylphenyl, or 3,4-diethyl-5-methylphenyl; a vinyl substituted phenyl, such as a 2-vinylphenyl, 3-vinylphenyl, 4-vinylphenyl, 3,4-divinylphenyl, or 3,5-divinylphenyl; a mixed vinylalkyl substituted phenyl group, such as a 3-ethyl-4-vinylphenyl, 3-vinyl-5- methylphenyl, 2,3-diethyl-4-vinylphenyl, 2-ethyl-3,5-divinylphenyl, or 3,5-dimethyl-4vinylphenyl; a biphenylyl, such as a 4-biphenylyl; a substituted biphenylyl, such as a 2-methyl4-biphenylyl, or 4'-methyl4-biphenylyl; a naphthyl; and a substituted naphthyl group, such as a methylnaphthyl, or vinylnaphthyl. In addition to these, other examples of aryl groups of the triaryamine compound include the substituents expressed by the following structural formulas 1 to 8.

(Chemical Formula 4)

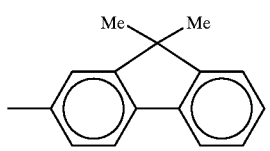

Structural Formula 1

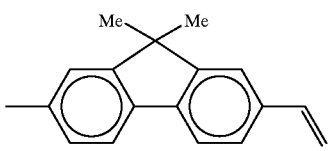

Structural Formula 2

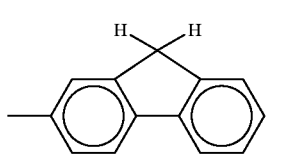

Structural Formula 3

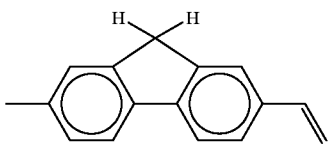

Structural Formula 4

Structural Formula 5
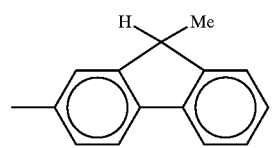

Structural Formula 6
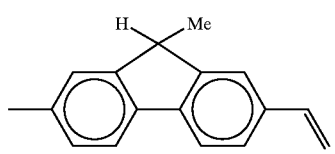

Structural Formula 7
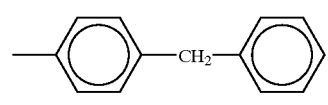

Structural Formula 8
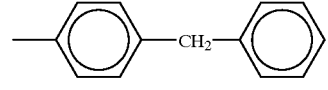

The above-mentioned aryl groups may also be bonded together, examples of which are a biphenyldiyl group, such as biphenyl-2,2'-diyl, 4,4'-dimethylbiphenyl-2,2'-diyl, 4-vinyl-4'-methylbiphenyl-2,2'-diyl, or other such biphenyldiyl group; and structures in which a plurality of aryl groups having methyl, ethyl, and vinyl substituents are bonded together with a hydrocarbon crosslinking group such as a methylene group, dimethylene group, or trimethylene group.

Specific examples of the triarylamine compound having a vinyl group used in the present invention include a triarylamine having one vinyl group per molecule such as 4-(N,N-diphenylamino)styrene, 4-(N,N-di(4-methylphenyl)amino)styrene, or 4-(N,N-di(3,4-dimethylphenyl)amino)styrene; a triarylamine having two vinyl groups per molecule such as phenylbis(4-vinylphenyl)amine, (4-methylphenyl)bis(4-vinylphenyl) amine, or (3,4-dimethylphenyl)bis(4-vinylphenyl)amine; a triarylamine having three vinyl groups per molecule such as tris(4-vinylphenyl)amine or tris(3-methyl-4-vinylphenyl) amine; and a triarylamine partially having a substituent expressed by one of the above Structural Formulas 1 to 8.

The following are examples of the triarylamine compound having a vinyl group which may be used in the present method.

(Chemical 5)

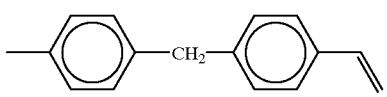

(VII)

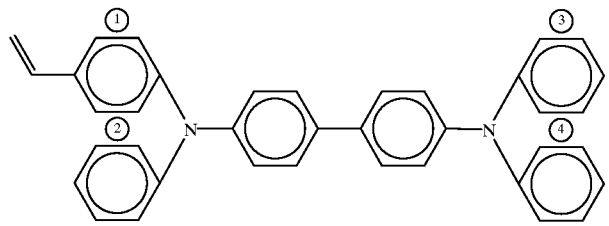

(VIII)

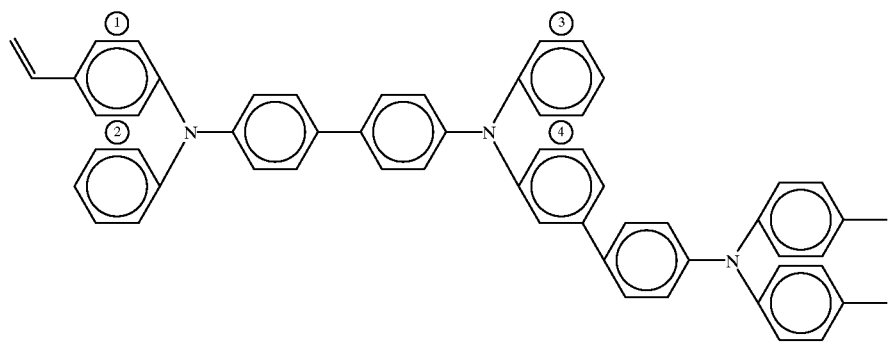

(IX)

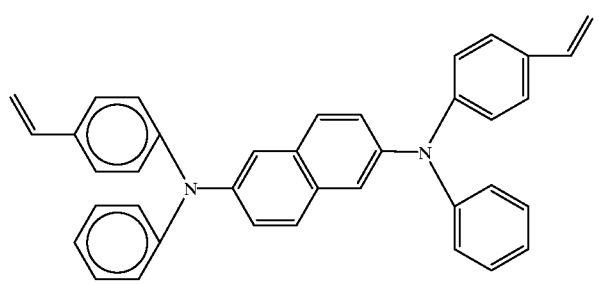

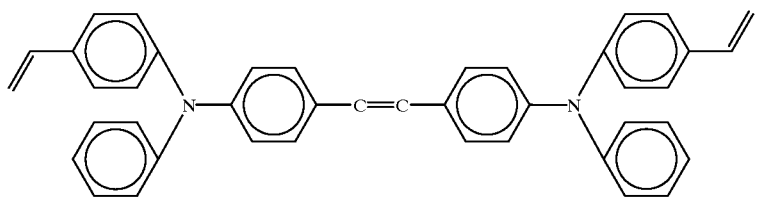

(X)

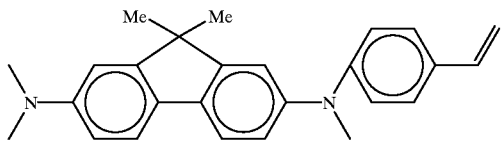

(XI)

For instance, the vinyl group in the above Formulas VII and VIII may be attached to the benzene rings of ② to ④. The position thereof may be the ortho, meta, or para position with respect to the nitrogen atom, but the para position is preferred because the reaction with the hydrido (hydrocarbonoxy)silane compound will proceed more easily. Similarly, in the case of a ring with two or more members, the vinyl group may be bonded to any of the carbon atoms that make up the ring, but it is preferable for it to be bonded to the constituent carbon atom farthest away from the nitrogen atom. Formula VIII illustrates the case of using a structure comprising a triarylamine that is additionally linked to two linked triarylamines as the triarylamine compound having a vinyl group used in the present method. A vinyl group may also be attached to this additionally linked triarylamine. Also, as shown in Formula IX, the bonding of two triarylamines may have a condensed ring structure as with naphthalene and there are no particular restrictions on this bonding of the two triarylamines which may be as shown in Formula X or XI.

Still other examples of the triarylamine compound having a vinyl group which may be used in the present method are given below.

(Chemical Formula 6)

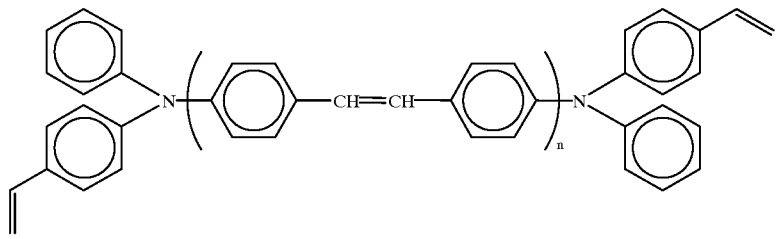

(XII)

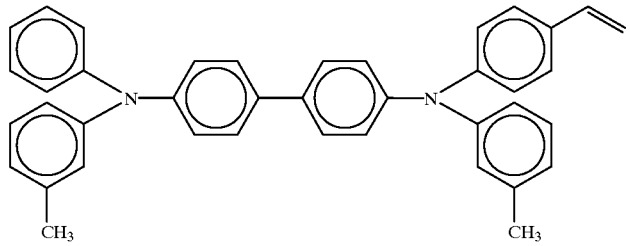

(Oxidation potential: 0.78 V)
Ionization potential: 5.42 eV (XIII)

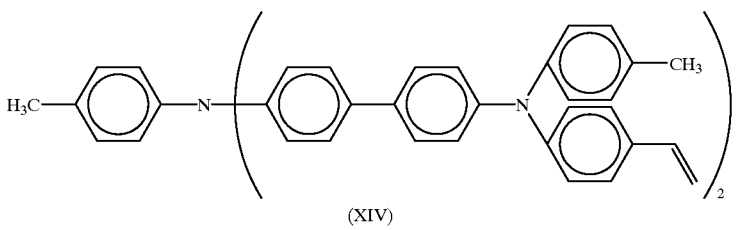

(XIV)

(Chemical Formula 7)
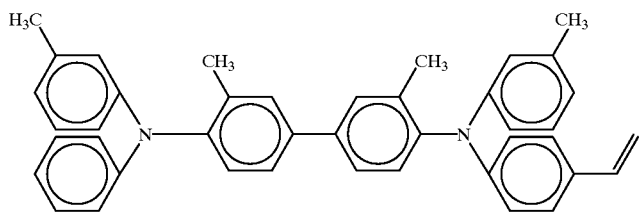
(Chemical Formula 8)
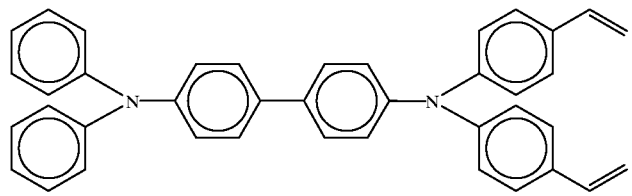
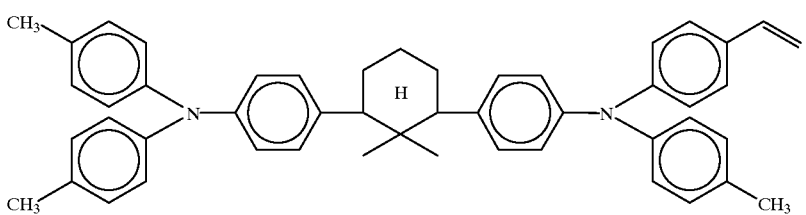
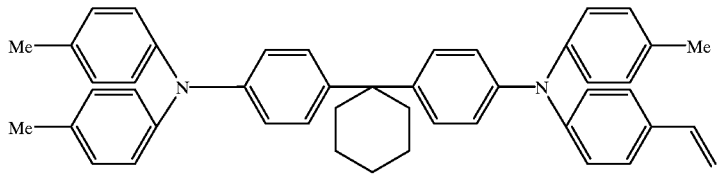
(Oxidation potential: 0.75 V)
Ionization potential: 5.40 eV
(Chemical Formula 9)
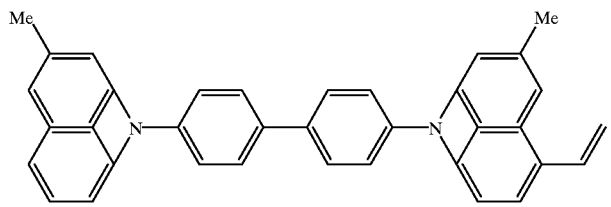
(Oxidation potential: 0.76 V)
Ionization potential: 5.40 eV
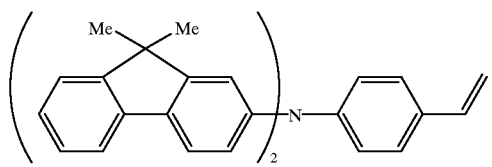
(Oxidation potential: 0.77 V)
Ionization potential: 5.41 eV
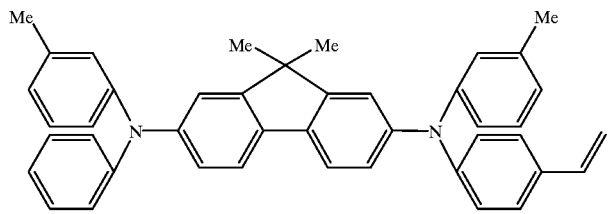

(Oxidation potential: 0.89 V)
Ionization potential: 5.28 eV (Chemical Formula 10)

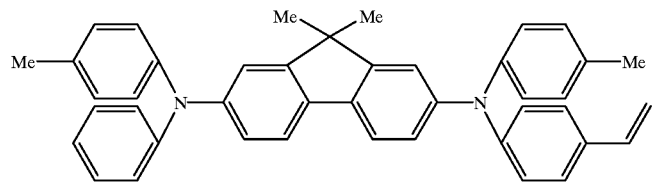

(Oxidation potential: 0.62 V)
Ionization potential: 5.27 eV

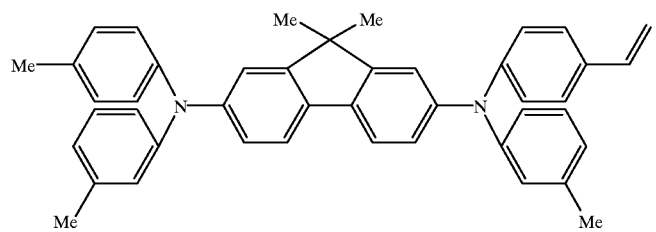

(Oxidation potential: 0.58 V)
Ionization potential: 5.22 eV

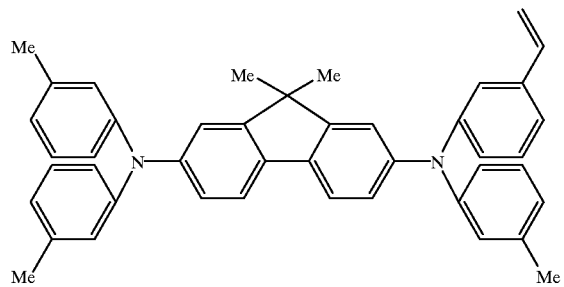

(Oxidation potential: 0.58 V)
Ionization potential: 5.23 eV

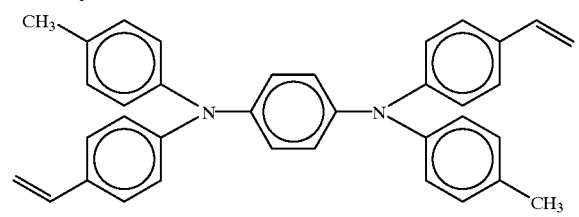

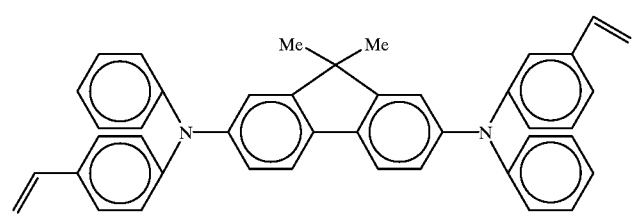

Description of Platinum or Platinum Compound Catalyst

The platinum or platinum compound catalyst of the present method can be selected from among platinum metal and platinum compounds and complexes thereof where the platinum has a negative electrical charge or is zero-valent, divalent, or tetravalent. The catalyst can be platinum-carrying microparticles and platinum colloids. Specific examples of complexes having a negative electrical charge include platinum carbonyl cluster anion compounds, such as $(Pt_3(CO)_6)^{2-}$, $(Pt_3(CO)_6)_2^{2-}$, and $(Pt_3(CO)_6)_4^{2-}$ (J Amer. Chem. Soc., 1976, 98, 7225); examples of zero-valent platinum compounds include a platinum (0) divinyltetramethyldisiloxane complex, a platinum (0) ethylene complex, and a platinum (0) styrene complex; examples of divalent platinum compounds include $Pt(II)Cl_2$, $Pt(II)Br_2$, bis(ethylene)$Pt(II)Cl_2$, (1,5-cyclooctadiene)$Pt(II)Cl_2$, platinum (II) acetylacetonate, and bis(benzonitrile)$Pt(II)Cl_2$; and examples of tetravalent platinum compounds include $Pt(IV)Cl_4$, $H_2Pt(IV)Cl_6$, $Na_2Pt(IV)Cl_6$, and $K_2Pt(IV)Cl_6$. Platinum-carrying microparticles include platinum carried on activated carbon, platinum carried on alumina, and platinum carried on silica. Of these, a platinum (0) divinyltetramethyldisiloxane complex or alcoholic solution of chloroplatinic acid is preferred from the standpoints of solubility in organic solvents, stability of the catalyst solution, and other usage aspects.

The amount of platinum required for a hydrosilylation reaction of a specific amount of substrate is related to the type of substrate, the reaction temperature, the reaction time, and other such factors, and as such cannot be unconditionally set forth. But generally, $10^{-3}$ to $10^{-8}$ mol of platinum can be used per mole of the hydrido (hydrocarbon oxy)silane compound, and using between $10^{-4}$ and $10^{-7}$ mol is preferable from the standpoints of the cost of the catalyst and the reaction time.

Description of Carboxylic Acid Compound The carboxylic acid compound used in the present invention can be any of the following (a), (b), (c), and (d).

(a) A carboxylic acid, there are no particular restrictions as long as it has carboxyl groups. Examples include saturated carboxylic acids, unsaturated carboxylic acids, monocarboxylic acids, and dicarboxylic acids. A saturated or unsaturated aliphatic hydrocarbon group, aromatic hydrocarbon group, halogenated hydrocarbon group, hydrogen atom, or the like is usually selected as the portion other than the carboxyl groups in these carboxylic acids.
(b) An anhydride of a carboxylic acid
(c) A silylated carboxylic acid
(d) A substance that will produce the above-mentioned carboxylic acid compounds of (a), (b), or (c) through a reaction or decomposition in the course of the hydrosilylation reaction in the present method.

The carboxylic acid compound must be present in the present method while the hydrosilylation reaction occurs, so it must be added to the method before the start of the hydrosilylation reaction or at some point up to the initial stage of the reaction.

As mentioned above, a carboxylic acid, a silylated carboxylic acid, or an anhydride of a carboxylic acid is suitable as the carboxylic acid compound used in the present method, but it is also acceptable to use a substance that will produce one of the above-mentioned carboxylic acid compounds through a reaction or decomposition in the present method. Specific examples of carboxylic acids include saturated monocarboxylic acids such as formic acid, acetic acid, propionic acid, n-butyric acid, isobutyric acid, hexanoic acid, cyclohexanoic acid, lauric acid, and stearic acid; saturated dicarboxylic acids such as oxalic acid and adipic acid; aromatic carboxylic acids such as benzoic acid and paraphthalic acid; carboxylic acids in which the hydrogen atoms of the hydrocarbon groups of these carboxylic acids have been substituted with a halogen atom or an organosilyl group such as chloroacetic acid, dichloroacetic acid, trifluoroacetic acid, para-chlorobenzoic acid, and trimethylsilylacetic acid; unsaturated fatty acids such as acrylic acid, methacrylic acid, and oleic acid; and compounds having hydroxy groups, carbonyl groups, or amino groups in addition to carboxyl groups, for example, hydroxy acids such as lactic acid, keto acids such as acetoacetic acid, aldehyde acids such as glyoxylic acid, and amino acids such as glutamic acid.

Specific examples of silylated carboxylic acids include trialkylsilylated carboxylic acids such as trimethylsilyl formate, trimethylsilyl acetate, triethylsilyl propionate, trimethylsilyl benzoate, and trimethylsilyl trifluoroacetate; and di-, tri-, and tetracarboxysilylates, such as dimethyldiacetoxysilane, diphenyldiacetoxysilane, methyltriacetoxysilane, vinyltriacetoxysilane, and silicon tetrabenzoate.

Examples of anhydrides of carboxylic acids include acetic anhydride, propionic anhydride, and benzoic anhydride. Examples of substances that produce one of the above-mentioned carboxylic acid compounds through a reaction or decomposition in the method include acetyl chloride, butyryl chloride, benzoyl chloride, and other carboxylic acid halides; carboxylic acid metal salts such as zinc acetate and thallium acetate; and carboxylic esters that are decomposed by light or heat such as (2-nitrobenzyl) propionate.

It is preferable for the carboxylic acid compound to be selected from the group consisting of carboxylic acids and silylated carboxylic acids.

The carboxylic acid compound can be used effectively by being added to the present method in an amount of 0.001 to 20 Wt. %, but for the purpose of achieving a good effect and using the compound efficiently an amount between 0.01 and 5 Wt. % should be added. The weight percent of carbonxylic acid compound added to the present method is based upon the total weight of the mixture composed of the hydrido (hydrocarbonoxy)silane compound, the triarylamine compound having a vinyl group, the platinum or platinum compound catalyst, and the carboxylic acid compound.

The temperature at which the reaction of the present method can be conducted should be between about 0 and 300° C., but a range of about 30 to 250° C. is preferred in terms of achieving a good reaction velocity and the stability of the product and the substrate participating in the reaction.

There is no fundamental need to use a solvent in the present method, but a hydrocarbon solvent, an oxygen-containing organic solvent, silicone, or the like can be used as a solvent for the catalyst component in order to facilitate the addition of the catalyst component, to control the reaction system temperature, or to dissolve the substrates. Examples of solvents that are useful for this purpose include saturated or unsaturated hydrocarbon compounds, such as hexane, cyclohexane, heptane, octane, dodecane, benzene, toluene, xylene, and dodecylbenzene; halogenated hydrocarbon compounds, such as chloroform, methylene chloride, chlorobenzene, and ortho- dichlorobenzene; ethers; esters; and silicones, such as double-terminated trimethylsilylpolydimethylsiloxane and hexamethyldisiloxane.

When the triarylamine having a hydrocarbonoxysilyl group manufactured by the present method is used as a charge transfer material, the ionization potential thereof should be between 4.5 and 6.2 eV. For this usage purpose, it is undesirable for the ionization potential to be less than 4.5 eV because the charge transfer material will be susceptible to oxidation and will therefore tend to be degraded. It is also undesirable for the ionization potential to exceed 6.2 eV because hole injection from the charge generation layer will tend not to occur and there will be a decrease in sensitivity.

The preferred triarylamine having a hydrocarbonoxysilyl group obtained by the present method has a structure in which the hydrocarbonoxysilyl group is bonded to an aromatic ring via an ethylene group. This is called a β-adduct with respect to the aromatic ring. An α-adduct with respect to the aromatic ring is also produced as a by-product.

The present invention will now be described in further detail through working examples, but the present invention is not limited to or by these examples. In the discussion of the characteristics of the products in the following examples GC-MS refers to gas chromatograph-mass spectrometry analysis. The "conversion rate" refers to the amount of triarylamine having a vinyl group reacted, and "yield" refers to the proportional production of product versus the amount of triarylamine having a vinyl group added to the method.

The hydrido (hydrocarbonoxy)silane compounds, alkylsilane compounds, and siloxane compounds used in these examples were all commercially available products or were synthesized by standard known methods. The unsaturated compounds were used in "as-purchased" form. Working examples and comparative examples will now be given in order to explain the technology of the present invention. In these working and comparative examples, DTAS, DXAS, DVBZ, and TVBZ stand for the following. For the sake of reference, the chemical formulas are given for the latter two.

DTAS: 4-(N,N-di(4-tolyl)amino)styrene
DXAS: 4-(N,N-di(3,4-xylyl)amino)styrene
DVBZ: N,N'-diphenyl-N,N'di(4-vinylphenyl)benzidine
TVBZ: N-phenyl-N,N',N'-tri(4-vinylphenyl)benzidine (Chemical Formula 11)

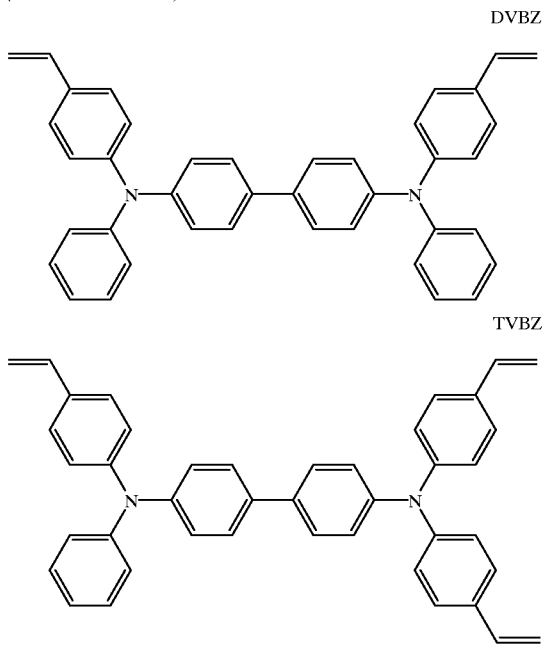

Working Example 1 (reaction between DXAS and triethoxysilane using a platinum catalyst in the presence of acetic acid). 0.5 g Of a toluene solution of DXAS (0.1 g of DXAS dissolved in 0.4 g of toluene) and 93 mg of triethoxysilane were added to a glass reaction tube and then 0.001 ml of acetic acid was added. To this was added 0.005 ml of a toluene solution of a zero-valent platinum complex of divinyltetramethyldisiloxane (platinum content: 0.4 Wt. %). The reaction tube was sealed with Teflon tape, placed in a 50° C. oil bath, and heated for 30 minutes. After cooling, the tube contents were analyzed by GC-MS, which revealed that the DXAS conversion rate was 99% and the β-adduct of triethoxysilane to DXAS was produced at a yield of 90% and the α-adduct at 1%.

Working Example 2 (reaction between DXAS and triethoxysilane using a platinum catalyst in the presence of formic acid). 0.5 g Of a toluene solution of DXAS (0.1 g of DXAS dissolved in 0.4 g of toluene) and 70 mg of triethoxysilane were added to a glass reaction tube and 0.001 ml of formic acid was added. To this was added 0.005 ml of a toluene solution of a zero-valent platinum complex of divinyltetramethyldisiloxane (platinum content: 0.4 Wt. %). The reaction tube was sealed with Teflon tape, placed in a 50° C. oil bath, and heated for 1 hour. After cooling, the tube contents were analyzed by GC-MS, which revealed that the DXAS conversion rate was 98%, and the β-adduct of triethoxysilane to DXAS was produced at a yield of 85% and the α-adduct at 2.3%.

Working Example 3 (reaction between DXAS and triethoxysilane using a platinum catalyst in the presence of trifluoroacetic acid). 0.5 g Of a toluene solution of DXAS (0.1 g of DXAS dissolved in 0.4 g of toluene) and 70 mg of triethoxysilane were added to a glass reaction tube and 0.001 ml of trifluoroacetic acid was added. To this was added 0.01 ml of a toluene solution of a zero-valent platinum complex of divinyltetramethyldisiloxane (platinum content: 0.2 Wt. %). The reaction tube was sealed with Teflon tape, placed in a 50° C. oil bath, and heated for 30 minutes. After cooling, the tube contents were analyzed by GC-MS, which revealed that the DXAS conversion rate was 98%, and the β-adduct of triethoxysilane to DXAS was produced at a yield of 77% and the α-adduct at 9.5%.

Working Example 4 (reaction between DXAS and triethoxysilane using a platinum catalyst in the presence of benzoic acid). 0.5 g Of a toluene solution of DXAS (0.1 g of DXAS dissolved in 0.4 g of toluene) and 70 mg of triethoxysilane were added to a glass reaction tube and 1.7 mg of benzoic acid were added. To this was added 0.01 ml of a toluene solution of a zero-valent platinum complex of divinyltetramethyldisiloxane (platinum content: 0.2 Wt. %). The reaction tube was sealed with Teflon tape, placed in a 50° C. oil bath, and heated for 30 minutes. After cooling, the tube contents were analyzed by GC-MS, which revealed that the DXAS conversion rate was 94%, and the β-adduct of triethoxysilane to DXAS was produced at a yield of 86% and the α-adduct at 1.1%.

Working Example 5 (reaction between DXAS and triethoxysilane using a platinum catalyst in the presence of methyltriacetoxysilane). 0.5 g Of a toluene solution of DXAS (0.1 g of DXAS dissolved in 0.4 g of toluene) and 70 mg of triethoxysilane were added to a glass reaction tube and 1.5 mg of methyltriacetoxysilane were added. To this was added 0.01 ml of a toluene solution of a zero-valent platinum complex of divinyltetramethyldisiloxane (platinum content: 0.2 Wt. %). The reaction tube was sealed with Teflon tape, placed in a 50° C. oil bath, and heated for 30 minutes. After cooling, the tube contents were analyzed by GC-MS, which revealed that the DXAS conversion rate was 91%, and the β-adduct of triethoxysilane to DXAS was produced at a yield of 84% and the α-adduct at 2.7%.

Working Example 6 (reaction between DXAS and trimethoxysilane using a platinum catalyst in the presence of acetic acid). 0.5 g Of a toluene solution of DXAS (0.1 g of DXAS dissolved in 0.4 g of toluene) and 53 mg of trimethoxysilane were added to a glass reaction tube and 0.005 ml of acetic acid was added. To this was added 10 μL of a toluene solution of a zero-valent platinum complex of divinyltetramethyldisiloxane (platinum content: 0.4 Wt. %). The reaction tube was sealed with Teflon tape, placed in a 50° C. oil bath, and heated for 30 minutes. After cooling, the contents were analyzed by GC-MS which revealed that the DXAS conversion rate was 95%, and the β-adduct of trimethoxysilane to DXAS was produced at a yield of 89.2% and the α-adduct at 1.0%.

Working Example 7 (reaction between DXAS and methyldimethoxysilane using a platinum catalyst in the presence of acetic acid). 430 mg Of a toluene solution of DXAS (95 mg of DXAS dissolved in 335 mg of toluene) and 106 mg of methyldimethoxysilane were added to a glass reaction tube and 0.002 ml of acetic acid was added. To this was added 0.005 ml of a toluene solution of a zero-valent platinum complex of divinyltetramethyldisiloxane (platinum content: 0.4 Wt. %). The reaction tube was sealed with Teflon tape, placed in a 41 ° C. oil bath, and heated for 30 minutes. After cooling, the tube contents were analyzed by GC-MS, which revealed that the DXAS conversion rate was 93% and the β-adduct of methyldimethoxysilane to DXAS was produced at a yield of 89.8% and the α-adduct at 1.6%.

Working Example 8 (reaction between DTAS and triethoxysilane using a platinum catalyst in the presence of acetic acid). 765 mg Of a toluene solution of DTAS (255 mg of DTAS dissolved in 510 mg of toluene) and 200 mg of triethoxysilane were added to a glass reaction tube and 0.002 ml of acetic acid was added. To this were added 0.006 ml of a toluene solution of a zero-valent platinum complex of divinyltetramethyldisiloxane (platinum content: 0.2 Wt. %). The reaction tube was sealed with Teflon tape, placed in a 50° C. oil bath, and heated for 30 minutes. After cooling, the tube contents were analyzed by GC-MS, which revealed that the DTAS conversion rate was 63% and the β-adduct of triethoxysilane to DTAS was produced at a yield of 61% and the α-adduct at 0.1%.

Working Example 9 (reaction between DXAS and triethoxysilane using a platinum chloride catalyst in the presence of cyclohexanecarboxylic acid). 0.5 g Of a toluene solution of DXAS (0.1 g of DXAS/0.4 g of toluene) and 70 mg of triethoxysilane were added to a glass reaction tube and 0.9 mg of cyclohexanecarboxylic acid was added. To this was added 0.01 ml of a toluene solution of a platinum chloride complex (platinum content: 0.08 Wt. %). The reaction tube was sealed with Teflon tape, placed in a 50° C. oil bath, and heated for 30 minutes. After cooling, the tube contents were analyzed by GC-MS, which revealed that the DXAS conversion rate was 88% and the β-adduct of methyldimethoxysilane to DXAS was produced at a yield of 68.6% and the α-adduct at 2.4%.

Working Example 10 (reaction between DXAS and triethoxysilane using a platinum catalyst in the presence of benzoic acid and an argon atmosphere). 2.5 g Of a toluene solution of DXAS (0.5 g of DXAS dissolved in 2.0 g of toluene) and 350 mg of triethoxysilane were added to an argon-purged flask and 2.9 mg of benzoic acid was added. To this was added 0.02 ml of a toluene solution of a zero-valent platinum complex of divinyltetramethyldisiloxane (platinum content: 0.4 Wt. %). The flask was placed in a 50° C. oil bath and heated for 30 minutes. After cooling, the flask contents were analyzed by GC-MS, which revealed that the DXAS conversion rate was 98% and the β-adduct of triethoxysilane to DXAS was produced at a yield of 92% and the α-adduct at 1.9%.

Comparative Example 1 (reaction between DXAS and triethoxysilane using a platinum catalyst with no carboxylic acid compound added). 0.5 g Of a toluene solution of DXAS (0.1 g of DXAS dissolved in 0.4 g of toluene) and 70 mg of triethoxysilane were added to a glass reaction tube and 0.018 ml of a toluene solution of a zero-valent platinum complex of divinyltetramethyldisiloxane (platinum content: 0.04 Wt. %) was added. The reaction tube was sealed with Teflon tape, placed in a 50° C. oil bath, and heated for 30 minutes. After cooling, the tube contents were analyzed by GC-MS which revealed that the DXAS conversion rate was 20% and the β-adduct of triethoxysilane to DXAS was produced at a yield of 9.2% and the α-adduct at 7.8%.

Comparative Example 2 (reaction between DXAS and trimethoxysilane using a platinum catalyst with no carboxylic acid compound added). 0.5 g Of a toluene solution of DXAS (0.1 g of DXAS dissolved in 0.4 g of toluene) and 53 mg of trimethoxysilane were added to a glass reaction tube and 0.01 ml of a toluene solution of a zero-valent platinum complex of divinyltetramethyldisiloxane (platinum content: 0.04 Wt. %) was added. The reaction tube was sealed with Teflon tape, placed in a 50° C. oil bath, and heated for 30 minutes. After cooling, the tube contents were analyzed by GC-MS, which revealed that the DXAS conversion rate was 2.5% and the β-adduct of trimethoxysilane to DXAS was produced at a yield of 1.0% and the α-adduct at 1.0%.

Comparative Example 3 (reaction between DXAS and methyldimethoxysilane using a platinum catalyst with no carboxylic acid compound added). 430 mg Of a toluene solution of DXAS (95 mg of DXAS dissolved in 335 mg of toluene) and 106 mg of methyldimethoxysilane were added to a glass reaction tube and 0.005 ml of a toluene solution of a zero-valent platinum complex of divinyltetramethyldisiloxane (platinum content: 0.4 Wt. %) was added. The reaction tube was sealed with Teflon tape, placed in a 41° C. oil bath, and heated for 30 minutes. After cooling, the tube contents were analyzed by gas chromatograph, which revealed that the DXAS conversion rate was 51% and the β-adduct of methyldimethoxysilane to DXAS was produced at a yield of 15.4% and the α-adduct at 31.9%.

Comparative Example 4 (reaction between DXAS and triethoxysilane using a platinum chloride catalyst with no carboxylic acid compound added). 0.5 g Of a toluene solution of DXAS (0.1 g of DXAS dissolved in 0.4 g of toluene) and 70 mg of triethoxysilane were added to a glass reaction tube and 0.01 ml of an ethanol/toluene solution of a platinum chloride complex (platinum content: 0.08 Wt. %) was added. The reaction tube was sealed with Teflon tape, placed in a 50° C. oil bath, and heated for 30 minutes. After cooling, the tube contents were analyzed by GC-MS, which revealed that the DXAS conversion rate was 57% and the β-adduct of triethoxysilane to DXAS was produced at a yield of 16.8% and the α-adduct at 22.2%.

Comparative Example 5 (reaction between DXAS and triethoxysilane using a platinum catalyst with no carboxylic acid compound added). 0.5 g Of a toluene solution of DXAS (0.1 g of DXAS dissolved in 0.4 g of toluene) and 70 mg of triethoxysilane were added to a glass reaction tube and 0.01 ml of a toluene solution of a zero-valent platinum complex of divinyltetramethyldisiloxane (platinum content: 0.2 Wt. %) was added. The reaction tube was sealed with Teflon tape, placed in a 50° C. oil bath, and heated for 30 minutes. After cooling, the tube contents were analyzed by GC-MS, which revealed that the DXAS conversion rate was 44% and the β-adduct of triethoxysilane to DXAS was produced at a yield of 14% and the α-adduct at 16%.

Comparative Example 6 (reaction between DXAS and triethoxysilane using a platinum catalyst, under argon, with no carboxylic acid compound added). 2.5 g Of a toluene solution of DXAS (0.5 g of DXAS dissolved in 2.0 g of toluene) and 350 mg of triethoxysilane were added to an argon purged flask and 0.02 ml of a toluene solution of a zero-valent platinum complex of divinyltetramethyldisiloxane (platinum content: 0.4 Wt. %) was added. The flask was placed in a 50° C. oil bath and heated for 30 minutes. After cooling, the flask contents were analyzed by GC-MS, which revealed that the DXAS conversion rate was 10% and the β-adduct of triethoxysilane to DXAS was produced at a yield of 4.3% and the α-adduct at 3%.

Comparative Example 7 (reaction between DTAS and triethoxysilane using a platinum catalyst with no addition of a carboxylic acid compound). 765 mg Of a toluene solution of DTAS (255 mg of DTAS dissolved in 510 mg of toluene) and 200 mg of triethoxysilane were added to a glass reaction tube and 0.006 ml of a toluene solution of a zero-valent platinum complex of divinyltetramethyldisiloxane (platinum content: 0.2 Wt. %) was added. The reaction tube was sealed with Teflon tape, placed in a 50° C. oil bath, and heated for 1 hour. After cooling, the tube contents were analyzed by GC-MS, which revealed that the DTAS conversion rate was 2.1% and the β-adduct and α-adduct of triethoxysilane to DTAS were each produced at a yield of 1.0%.

Working Example 11 (reaction between DVBZ and triethoxysilane using a platinum catalyst in the presence of acetic acid). 100 mg Of DVBZ, 90 mg of triethoxysilane, and 0.150 ml of toluene were added to a glass reaction tube and 0.001 ml of acetic acid was added. To this was added 0.006 ml of an isopropyl alcohol/toluene solution of a zero-valent platinum complex of divinyltetramethyldisiloxane (platinum content: 0.04 Wt. %). The reaction tube was sealed with Teflon tape, placed in a 50° C. oil bath, and heated for 1 hour. After cooling, the tube contents were analyzed by GPC, which revealed that the DVBZ conversion rate was 99% and the monosilylation product was produced at a yield of 17% and the disilylation product at 82%. No peak for α-silylate product was seen in the $^{29}$Si-NMR spectrum of this sample.

Comparative Example 8 (reaction between DVBZ and triethoxysilane using a platinum catalyst with no carboxylic acid compound added). 100 mg Of DVBZ, 90 mg of triethoxysilane, and 0.150 ml of toluene were added to a glass reaction tube and 0.006 ml of an isopropyl alcohol-toluene solution of a zero-valent platinum complex of divinyltetramethyldisiloxane (platinum content: 0.04 Wt. %) was added. The reaction tube was sealed with Teflon tape, placed in a 50° C. oil bath, and heated for 1 hour. After cooling, the tube contents were analyzed by GPC, which revealed that the DVBZ conversion rate was 76% and the monosilylation product was produced at a yield of 43% and the disilylation product at 23%. According to the $^{29}$Si-NMR spectrum of this sample, the ratio of α-silylate to β-silylate was 1:2.

Working Example 12 (reaction between DVBZ and methyldimethoxysilane using a platinum catalyst in the presence of acetic acid). 100 mg Of DVBZ, 60 mg of methyldimethoxysilane, and 0.150 ml of toluene was added to a glass reaction tube and 0.001 ml of acetic acid was added. To this was added 0.006 ml of an isopropyl alcohol/toluene solution of a zero-valent platinum complex of divinyltetramethyldisiloxane (platinum content: 0.04 Wt. %). The reaction tube was sealed with Teflon tape, placed in a 50° C. oil bath, and heated for 1 hour. After cooling, the tube contents were analyzed by GPC, which revealed that the DVBZ conversion rate was 96% and the monosilylation product was produced at a yield of 31% and the disilylation product at 64%. No peak for α-silylate product was seen in the $^{29}$Si-NMR spectrum of this sample.

Comparative Example 9 (reaction between DVBZ and methyldimethoxysilane using a platinum catalyst with no carboxylic acid compound added). 100 mg Of DVBZ, 90 mg of methyldimethoxysilane, and 0.15 ml of toluene were added to a glass reaction tube and 0.006 ml of an isopropyl alcohol/toluene solution of a zero-valent platinum complex of divinyltetramethyldisiloxane (platinum content: 0.04 Wt. %) was added. The reaction tube was sealed with Teflon tape, placed in a 50° C. oil bath, and heated for 1 hour. After cooling, the tube contents were analyzed by GPC, which revealed that the DVBZ conversion rate was 62%, the monosilylation product was produced at a yield of 38%, the disilylation product at 14%, and polymer at 9%. According to the $^{29}$Si-NMR spectrum of this sample, the ratio of α-silylated product to β-silylated product was 1:2.

We claim:

1. A method for making a triarylamine compound having hydrocarbonoxysilyl groups comprising reacting a hydrido (hydrocarbonoxy)silane described by formula

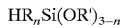

with a triarylamine compound having at least one triarylamine structure per molecule described by formula

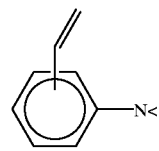

in the presence of platinum or platinum compound catalyst and a carboxylic acid compound; where each R is an independently selected hydrocarbon group selected from the group consisting of hydrocarbon groups comprising 1 to 10 carbon atoms and hydrocarbon groups comprising 1 to 10 carbon atoms having at least one of the carbon atoms bonded to a hetero-atom selected from the group consisting of O, N, F, Cl, Br, I, S, and Si; each R' is an independently selected hydrocarbon group comprising 1 to 10 carbon atoms; and n=0, 1, or 2, where the other bonds of the nitrogen atom are bonded to an aryl group.

2. A method according to claim 1, where each R and R' is an independently selected alkoxy group comprising 1 to 10 carbon atoms.

3. A method according to claim 1, where the hydrido (hydrocarbonoxy)silane compound is an alkoxysilane.

4. A method according to claim 1, where the hydrido (hydrocarbonoxy)silane compound is selected from the group consisting of trimethoxysilane, triethoxysilane, and methyldimethoxysilane.

5. A method according to claim 1, where the triarylamine compound comprises one triarylamine structure having a vinyl group.

6. A method according to claim 1, where the triarylamine compound comprises two or more triarylamine structures having a vinyl group.

7. A method according to claim 1, where the triarylamine compound comprises at least one triarylamine structure having a vinyl group and at least one triarylamine structure without a vinyl group.

8. A method according to claim 1, where the triarylamine compound is selected from the group consisting of 4-(N,N-di(4-tolyl)amino)styrene, 4-(N,N-di(3,4-xylyl)amino) styrene, N,N'-diphenyl-N,N'-di(4-vinylphenyl)benzidine, and N-phenyl-N,N',N'-tri(4-vinylphenyl)benzidine.

9. A method according to claim 1, where the platinum or platinum compound catalyst is selected from the group consisting of platinum (0) divinyltetramethyldisiloxane complex and alcoholic solution of chloroplatinic acid.

10. A method according to claim 1, where the carboxylic acid compound is selected from the group consisting of carboxylic acid and silylated carboxylic acids.

11. A method according to claim 1, where the carboxylic acid is added in an amount of 0.001 to 20 Wt. %, based on the total weight of components added to the method.

12. A method according to claim 1, where the carboxylic acid is added in an amount of 0.01 to 5 Wt. %, based on the total weight of components added to the method.

13. A method according to claim 1, where the carboxylic acid is selected from the group consisting of acetic acid, formic acid, trifluoroacetic acid, benzoic acid, methyltriacetoxysilane, and cyclohexanecarboxylic acid.

14. A method according to claim 1, where the reaction is effected at a temperature within a range of about 30° C. to 250° C.

* * * * *